United States Patent

Dwyer et al.

[11] Patent Number: 5,125,922
[45] Date of Patent: Jun. 30, 1992

[54] METHOD FOR LASER SURGERY

[76] Inventors: Richard M. Dwyer, 201 S. Alvarado St., Ste. 407, Los Angeles, Calif. 90057; Douglas A. Pinnow, 25402 Spotted Pony La., Laguna Hills, Calif. 92653

[21] Appl. No.: 85,798

[22] Filed: Aug. 17, 1987

Related U.S. Application Data

[63] Continuation of Ser. No. 727,266, Apr. 25, 1985, abandoned.

[51] Int. Cl.⁵ .............................................. A61N 5/06
[52] U.S. Cl. ................................... 606/3; 606/2; 606/10; 606/13; 606/14; 606/17; 128/395; 128/397; 128/398
[58] Field of Search ............. 128/303.1, 362, 395–398

[56] References Cited

U.S. PATENT DOCUMENTS

| | | | |
|---|---|---|---|
| 4,240,431 | 12/1980 | Komiya | 606/15 |
| 4,249,533 | 2/1981 | Komiya | 606/15 |
| 4,266,547 | 5/1981 | Komiya | 606/15 |
| 4,273,127 | 6/1981 | Auth et al. | 128/303.1 |
| 4,311,142 | 1/1982 | Machida | 128/303.1 |
| 4,469,098 | 9/1984 | Davi | 128/303.1 |
| 4,520,816 | 6/1985 | Schachar et al. | 128/303.1 |
| 4,580,558 | 4/1986 | Cabrera et al. | 128/303.1 |
| 4,627,435 | 12/1986 | Hoskin | 128/303.1 |
| 4,633,866 | 1/1987 | Peyman et al. | 128/303.1 |

FOREIGN PATENT DOCUMENTS

| | | | |
|---|---|---|---|
| 2809007 | 9/1979 | Fed. Rep. of Germany | 128/395 |
| 8501445 | 4/1985 | World Int. Prop. O. | 128/395 |

OTHER PUBLICATIONS

Laser Surgery, edited by Issac Kaplan, Jerusalem Academic Press 1976 p. 150.
Laser Handbook vol. 1 edited by F. T. Arecchi and E. O. Schulz-Dubois pp. 356–362.
Lasers Cut A Swath In Surgical and Medical Applications, IEEE Spectrum, Mar. 1985, pp. 82–87 (entire article).

Primary Examiner—David M. Shay
Attorney, Agent, or Firm—Harris, Kern, Wallen & Tinsley

[57] ABSTRACT

Method and apparatus for tissue cutting and cauterizing using a YAG laser and an optical fiber. YAG laser outputs at wavelengths of 1.06 and 1.3 microns are used for tissue cauterizing and cutting, respectively. In one embodiment, a multimode laser with means for switching the laser output between the two wavelengths is utilized; in another embodiment, individual lasers operating at the respective wavelengths are utilized.

6 Claims, 1 Drawing Sheet

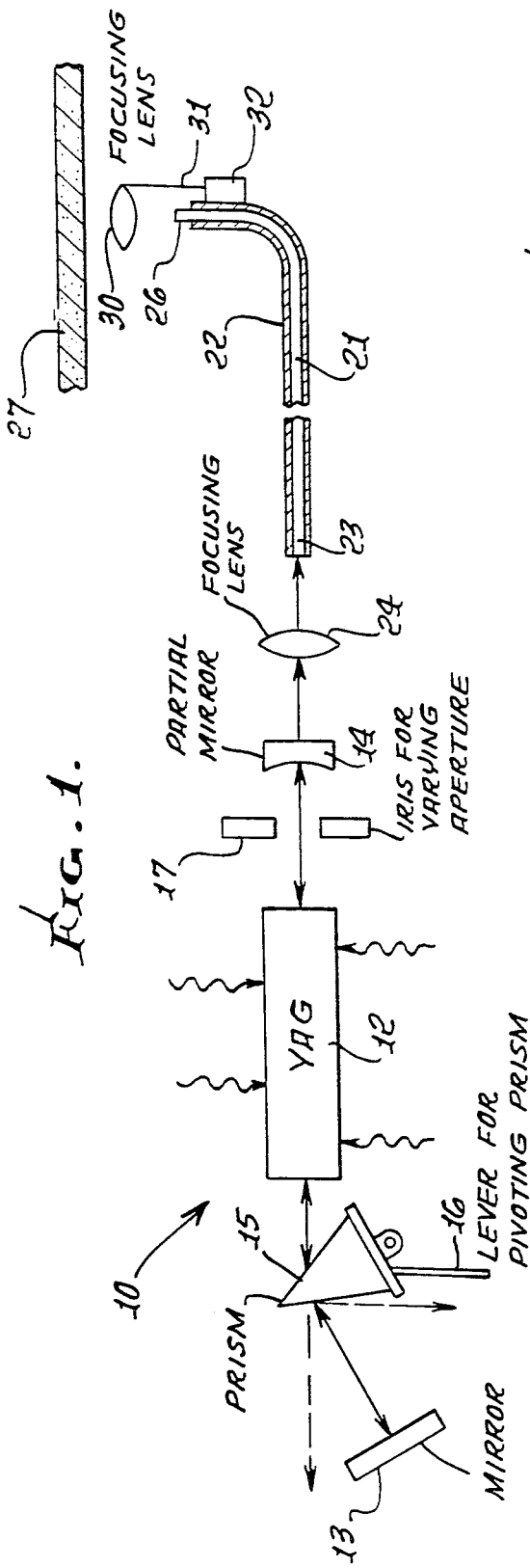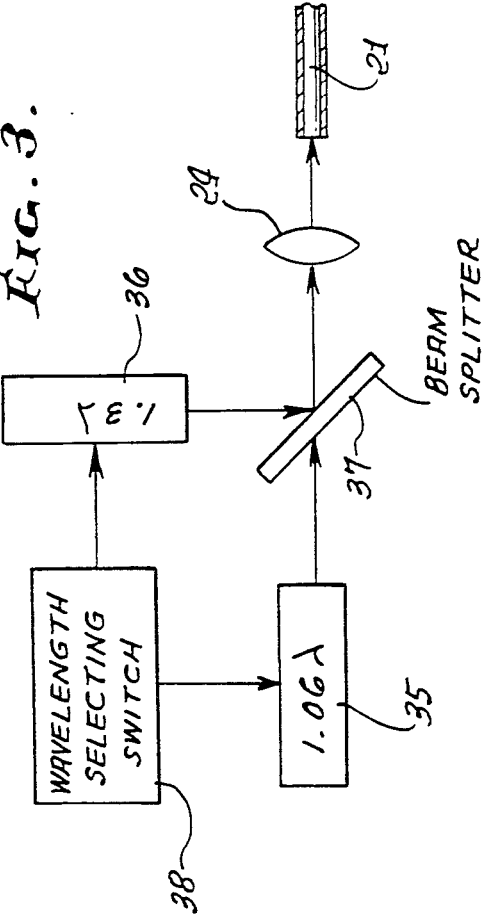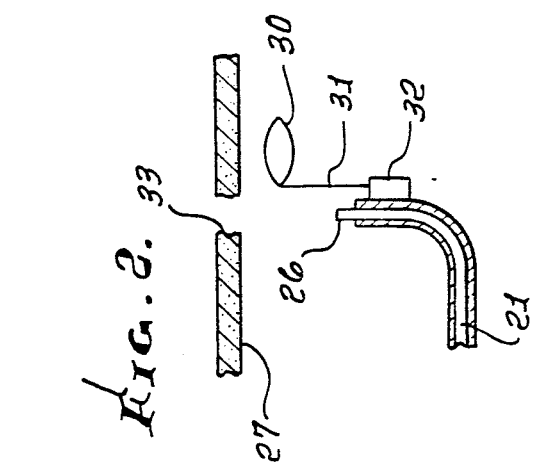

METHOD FOR LASER SURGERY

This application is a continuation of U.S. application Ser. No. 06/727,266, filed Apr. 25, 1985, now abandoned.

BACKGROUND OF THE INVENTION

This invention relates to cutting and cauterizing of body tissue by means of laser energy and in particular, to a new and improved method and apparatus for laser surgery utilizing a YAG laser and an optical fiber for delivery of the laser energy.

In the past, lasers have been utilized for surgical procedures. It is known to use the YAG laser at a wavelength of 1.06 microns to provide an output to an optical fiber for surgical cauterizing. However, this device has not been satisfactory for cutting of tissue. Also, it has been known to use the $CO_2$ laser in cutting procedures. However, there are no commercially available fibers that operate satisfactorily with the $CO_2$ laser, and therefore surgical uses of the $CO_2$ laser are severely limited.

It has long been known that it is highly desirable in surgical procedures for the surgeon to be able to easily cauterize tissue and to make precise tissue cuts during a surgical procedure in order to reduce bleeding and facilitate further surgical procedures, as well as to enhance healing. While this is true for external applications, it is especially so for surgery deep within the body. It is also desirable to be able to achieve these functions with a single surgical instrument so that the surgeon does not have to change tools during a procedure.

Accordingly, it is an object of the present invention to provide a new and improved method and apparatus for laser surgery which permits use of laser energy both for cutting and for cauterizing, with a single instrument with the change in function under the direct control of the surgeon, both outside the body and inside the body.

It is an additional object of the present invention to provide such a method and apparatus which can utilize an optical fiber for delivery of the energy, with the optical fiber having a small distal end which is readily manipulated and which can be utilized through an endoscope or other surgical instrumentation, as desired.

It is an object of the present invention to provide such a method and apparatus which can utilize conventional laser technology and conventional optical fiber techniques to provide a surgical instrument which is small, compact and easily manipulated and which is relatively inexpensive, while achieving the desired aims of substantially instantaneous changing between cutting and cauterizing functions.

Other objects, advantages, features and results will more fully appear in the course of the following description.

SUMMARY OF THE INVENTION

A method of surgery using a YAG laser and an optical fiber wherein energy from the laser at a wavelength of 1.06 microns is directed through the optical fiber to the tissue for cauterizing of tissue, and energy at a wavelength of 1.3 microns is directed through the fiber for cutting tissue.

The invention also includes laser surgical apparatus with either a single YAG laser selectively operating at 1.06 and 1.3 microns wavelength or two lasers operating at 1.06 and 1.3 microns, respectively, with the laser output directed through an optical fiber to the tissue to be treated. In its simplest form the apparatus of the invention comprises a dual wavelength YAG laser selectively operable at 1.06 and 1.3 microns wavelength with means operable by the surgeon for selecting the desired wavelength and means for directing the output toward tissue, with or without an optical fiber.

BRIEF DESCRIPTION OF THE DRAWINGS

FIG. 1 is a diagrammatic presentation of a multimode or multiwavelength YAG laser and optical fiber combination, incorporating the presently preferred embodiment of the invention;

FIG. 2 is a partial view similar to that of FIG. 1 showing an alternative configuration for the distal end of the optical fiber; and FIG. 3 is a view similar to that of FIG. 1 showing an alternative embodiment incorporating two lasers.

DESCRIPTION OF THE PREFERRED EMBODIMENTS

A laser is diagrammatically illustrated in FIG. 1, more specifically a $Nd:Y_3Al_5O_{12}$ laser 10, which is usually referred to as a YAG laser.

In the preferred embodiment illustrated, the laser 10 includes a YAG rod 12, a high reflecting mirror 13, a partially reflecting mirror 14, a pivotally mounted prism 15 with a lever 16 for pivoting the prism, and an iris 17 for varying the output aperture. The laser may be conventional in construction and includes a housing with pumping source, power supply and cooling source (not shown). The YAG laser operates at discrete spectral lines and will function at a number of different wavelengths. The wavelengths of interest for the present invention are at about 1.06 and 1.3 microns. The operating wavelengths for the YAG laser at room temperature are reported as including 1.0641, 1.319 and 1.338 microns. These are often referred to as 1.06, 1.32 and 1.34, respectively, and the figure 1.06 and 1.3 as used herein are intended to encompass these more precise figures.

In operation, the prism 15 functions to disperse radiation passing therethrough, in the conventional manner, and hence can be used to tune the operation of the laser to a particular wavelength by appropriately pivoting the prism. In one alternative embodiment, the highly reflecting mirror can be mounted directly on the face of the prism, and in another alternative embodiment, a diffraction grating may be utilized in place of the prism and mirror. The iris 17 may be used for controlling the size of the output aperture, and may be varied depending upon the operating wavelength desired. It is preferred to reduce the aperature when operating at 1.3 microns as this improves the single mode lasing and enhances beam concentration for cutting.

The surgical instrument also includes an optical fiber 21, preferably a silica fiber, and preferably enclosed in a protective sheath 22. While a single fiber is preferred, a bundle of fibers may be utilized, and the word "fiber" as used herein covers both the single fiber and the fiber bundle. In the embodiment of FIG. 1, the laser 10 and the proximal end 23 of the fiber 21 are mounted so that the output of the laser through the partial mirror 14 is directed onto the proximal end 23, preferably with a focusing lens 24. The distal end 26 of the fiber 21 is designed to be readily manipulatable for positioning at the tissue 27 to be treated. In one embodiment, the surgeon may manually grasp the fiber adjacent the distal end; in another embodiment, the fiber may be mounted in an endoscope and be remotely manipulated, in the conventional endoscope manner.

While the presently preferred embodiment of the surgical instrument and the surgical process utilizes an optical fiber as the element for delivering the laser output to the worksite, the optical fiber may be omitted, with the laser output being delivered by conventional output delivery devices. Also the distal end of the instrument, with or without the optical fiber, may be manipulated by an articulated arm and guided by the surgeon using a surgical microscope for viewing the worksite.

Another focusing lens 30 may be mounted at the distal end 26 for improved concentration of energy for the cutting procedure. As shown in FIG. 1, the lens 30 may be mounted on a shaft 31 which is carried in a bracket 32. The shaft 30 may rotate in the bracket to move the lens from a position in the optical path as shown in FIG. 1, to a position out of the optical path as shown in FIG. 2. Alternatively, the shaft 31 may translate in the bracket 32, moving the lens 30 toward and away from the distal end 26 of the fiber 21. When the lens 30 is incorporated in the instrument, the lens will be used to focus the energy to a small spot for the cutting operation, and will be moved to have a larger spot or an unfocused spot for the cauterizing procedure.

It has been found that YAG laser energy delivered through an optical fiber at a wavelength of about 1.06 microns is especially suited for surgical cauterizing of tissue because of its relatively deep penetration into tissue (several mm or more), but is not satisfactory for cutting at tissue. Hence, the 1.06 wavelength laser has not been suitable for many surgical procedures. Now it has been found that the same YAG laser with optical fiber when operating at a wavelength of about 1.3 microns is especially suitable for cutting tissue because its beam is absorbed in a fraction of a mm of tissue, while not being satisfactory for cauterizing tissue.

Hence, when in use for cauterizing tissue, the instrument of the present invention is operated at 1.06 microns by appropriate adjustment of the prism 15, and of the lens 30 when used, and the surgeon manipulates the distal end of the fiber as desired. However when a cutting procedure is desired, the surgeon changes the operating wavelength of the YAG laser to 1.3 microns, typically by a foot operated lever or manual switch, and immediately proceeds with the cutting of tissue using the same instrument without requiring any hand or head movements.

During use, the instrument is quickly switched back and forth between the 1.06 and the 1.3 micron wavelength, without requiring release of or movement of the distal end, thereby greatly enhancing the ease and quickness of the surgical procedure.

By using the process and apparatus of this invention for switching between coagulation or cauterizing and cutting, the surgeon can approach true "bloodless" surgery. The invention also provides a no touch technique for both cutting and coagulating. The instrument substantially reduces the degree and amount of manual mechanical dexterity required to complete the procedure, by using directed light energy instead of an interposing mechanical device, i.e. a scapel. Removal of a lesion or destruction of the lesion can be accomplished through a tiny incision using a narrow beam of light through a deep channel or hole too small for mechanical devices or hands, to coagulate the lesion and then remove it via converting the lesion to smoke, with the procedure therefore being less invasive.

FIG. 1 shows the distal end 26 of the fiber 21 directed to the surface of a portion of tissue 27, for cutting at the surface. FIG. 2 shows the distal end 26 positioned at a cut 33 in the tissue 27 for coagulation at the cut.

An alternative embodiment of the invention is shown in FIG. 3, which embodiment uses two YAG lasers 35, 36, with the laser 35 operating at 1.06 microns and the laser 36 operating at 1.3 microns wavelength. In one configuration the lasers 35, 36 are fixed in the instrument housing. The output of one laser, here the laser 35, is directed to the lens 24 through a beam splitter 37, and the output of the other laser is reflected through the lens 24 by the beam splitter 37. The respective lasers are turned on and off as desired by a wavelength selecting switch 38 operable by the surgeon.

We claim:

1. In a method of surgery using a YAG laser for reducing blood flow at the surgical site during a surgical cutting procedure, the steps of:
    directing energy from a YAG laser operating at about a 1.03 micron wavelength, to tissue to heat the tissue to a temperature at which tissue is destroyed for cutting the tissue;
    directing energy from a YAG laser operating at about a 1.06 micron wavelength, to the cut tissue for cauterizing the tissue; and
    repeating the cutting and cauterizing steps during the surgical procedure by repeatedly switching back and forth between the 1.3 micron and the 1.06 micron wavelengths.

2. The method of claim 1 utilizing a single laser and changing its wavelength between about 1.06 and about 1.3 microns.

3. The method of claim 1 utilizing two lasers and operating each at a single wavelength.

4. In a method of surgery using a YAG laser and an optical fiber for reducing blood flow at the surgical site during a surgical cutting procedure, the steps of:
    directing energy from a YAG laser operating at about a 1.3 micron wavelength, through the optical fiber to the tissue to heat the tissue to a temperature at which tissue is destroyed for cutting the tissue;
    directing energy from a YAG laser operating at about a 1.06 micron wavelength, through an optical fiber to the cut tissue for cauterizing the tissue; and
    repeating the cutting and cauterizing steps during the surgical procedure by repeatedly switching back and forth between the 1.3 micron and the 1.06 micron wavelengths.

5. The method of claim 1 utilizing a single laser and changing its wavelength between about 1.06 and about 1.3 microns.

6. The method of claim 1 utilizing two lasers and operating each at a single wavelength, and switching the input to the optical fiber from one laser to the other.

* * * * *